United States Patent
Lee

(10) Patent No.: US 9,289,523 B2
(45) Date of Patent: Mar. 22, 2016

(54) UNIVERSAL UV STERILIZER

(71) Applicant: Seoul Viosys Co., Ltd., Ansan-si (KR)

(72) Inventor: Chung Hoon Lee, Ansan-si (KR)

(73) Assignee: Seoul Viosys Co., Ltd., Ansan-si (KR)

( * ) Notice: Subject to any disclaimer, the term of this patent is extended or adjusted under 35 U.S.C. 154(b) by 0 days.

(21) Appl. No.: 14/516,458

(22) Filed: Oct. 16, 2014

(65) Prior Publication Data
US 2015/0102235 A1    Apr. 16, 2015

(30) Foreign Application Priority Data
Oct. 16, 2013   (KR) .......................... 10-2013-0123474

(51) Int. Cl.
*A61L 2/10*    (2006.01)
(52) U.S. Cl.
CPC ....................... *A61L 2/10* (2013.01)

(58) Field of Classification Search
USPC ............... 250/453.11, 454.11, 455.11, 493.1, 250/504 R, 504 H; 422/22, 24
See application file for complete search history.

(56) References Cited

U.S. PATENT DOCUMENTS

2002/0074559 A1*   6/2002   Dowling .................. A61N 5/06 257/99

* cited by examiner

*Primary Examiner* — Nicole Ippolito
(74) *Attorney, Agent, or Firm* — Perkins Coie LLP

(57) ABSTRACT

Disclosed is a UV sterilizer. The UV sterilizer includes a body including a top surface and a sidewall, at least one first UV LED chip disposed on the top surface of the body, and at least one second UV LED chip disposed on the sidewalls of the body. The body is freely movable among various target spaces to be sterilized, whereby the UV sterilizer can perform sterilization in a variety of spaces without being limited to a specific space.

23 Claims, 5 Drawing Sheets

UNIVERSAL UV STERILIZER

PRIORITY CLAIMS AND CROSS-REFERENCE TO RELATED APPLICATION

This patent document claims priority from and the benefit of Korean Patent Application No. 10-2013-0123474, filed on Oct. 16, 2013, the contents of which are hereby incorporated by reference in their entirety.

TECHNICAL FIELD

This patent document relates to a universal UV sterilizer using UV LEDs.

BACKGROUND

Ultraviolet (UV) light has been known to sterilize various microorganisms in air and transparent liquids. Short-Wave UV (UV-C) band is referred to as germicidal UV due to its sterilization effects. In sterilizers, mercury (Hg) lamps have been widely used as UV light sources, since Hg lamps emit UV light in a wavelength band of about 254 nm exhibiting excellent sterilization effects.

In recent years, there have been proposed technologies for including light emitting diodes (LEDs), emitting UV light in the UV-C band, in sterilizers. For example, Korean Patent Publication No. 10-2012-0009928 discloses an air cleaner using UV LEDs to have a sterilization function, and Korean Patent Publication No. 10-2011-0039985 discloses a UV sterilization washing machine to which an LED unit is mounted.

However, typical UV sterilizers are embedded in specific electronic appliances such as refrigerators, washing machines, humidifiers, vacuum cleaners, and the like. Therefore, the UV sterilization may only be possible for the specific electronic appliances that include the UV sterilizers, and may not be used for other electronic appliances.

SUMMARY

Embodiments of the technology disclosed in this patent document provide a UV sterilizer that can be used in a variety of spaces without being limited to a specific space or particular electronic appliances.

In addition, embodiments of the technology disclosed in this patent document provide a UV sterilizer that can be used not only in a large space but also in a small space.

In accordance with one aspect of the disclosed technology, a UV sterilizer is provided to include: a body including a top surface and a sidewall; at least one first UV LED chip disposed on the top surface of the body; and at least one second UV LED chip disposed on the sidewall of the body, wherein the body has cross-sectional areas gradually decreasing toward the top surface such that the sidewall is inclined, and a light emitting surface of the second UV LED chip is substantially parallel to a surface of the sidewall.

According to embodiments of the disclosed technology, the body is freely movable among various target spaces to be sterilized. The body can be easily moved to a variety of places, such as a refrigerator, a washing machine, a humidifier, a sink, a wardrobe, a shoe rack, and the like, where a UV sterilizer is frequently used, without being limited to a specific space. Thus, various spaces can be sterilized using one UV sterilizer. In some implementations, the UV LED chips can be arranged on the sidewall and the top surface of the body, thereby sterilizing a wide region using UV light.

In some implementations, the body can include a main body and a sub-body detachably coupled to the main body.

By having the main body and the sub-body, it is possible to sterilize any regions regardless of a size. The main body and the sub-body can perform sterilization while being detachably attached to each other, while the main body and the sub-body attached or detached corresponding to a size of a target space to be sterilized.

In some implementations, the main body can have a recess for accommodating the sub-body, the sub-body can be electrically connected to the main body within the recess of the main body, the first UV LED chip can be disposed on the sub-body, and the second UV LED chip can be disposed on the main body.

In some implementations, the sub-body can have a smaller width than the main body.

In some implementations, the sub-body can have a polygonal prismatic or cylindrical shape.

In some implementations, the UV sterilizer can further include an electric wire connected to the sub-body and supplying DC power to the first and second UV LED chips.

In some implementations, the UV sterilizer can further include a converter that converts high-voltage AC power into low-voltage DC power, wherein the converter can be disposed outside the sub-body and the electric wire can be connected to the converter.

Even when household AC power is used, the AC power is converted into low-voltage DC power by the converter. Therefore, it is possible to supply DC power of 75 V or lower through the electric wire.

In some implementations, the main body can have a slot passing through sidewall of the main body and connected to the recess, and the electric wire can be received in the slot when the sub-body is coupled to the main body.

The sub-body to which the electric wire is connected can be easily coupled to the main body through the slot.

In some implementations, the main body can further include a groove formed on an outer surface of the sidewall of the main body and extending from the slot.

In some implementations, the UV sterilizer can further include a battery disposed inside the sub-body and supplying DC power to the first and second UV LED chips.

In some implementations, the sub-body can include a magnet. The sub-body can be difficult to handle due to its small size, when detached from the main body. The magnet can be used to couple the small sub-body to a support member such as a metal rod, thereby facilitating handling of the sub-body.

In some implementations, the body can further include a receiver and a controller, and the receiver can receive signals from a remote controller separated from the body.

In some implementations, the UV sterilizer can further include an electric wire supplying DC power voltage of 75 V or lower to the first and second UV LED chips, and the electric wire can have a smaller thickness than a household cable.

In some implementations, the UV sterilizer can further include a battery supplying DC power to the first and second UV LED chips.

The portability of the body can be further enhanced by the use of the battery.

In some implementations, the UV sterilizer can further include a lens changing distribution of light of the second UV LED chip.

In some implementations, the lens can include a supporting member.

In some implementations, the lens can be detachable from the body.

In some implementations, the body can have a polygonal (e.g., quadrangular) frusto-pyramidal shape or a frusto-conical shape.

In another aspect, a UV sterilizer is provided to include: a body having a top surface and a sidewall shaped to fit in an area to be sterilized; an UV LED chip disposed on a top surface of the body and structured to emit UV light having an emission pattern to distribute the emitted UV light within the area to be sterilized; another UV LED chip disposed on a sidewall of the sub-body and structured to emit another UV light having another emission pattern to distribute the other emitted light within the area to be sterilized, wherein at least one of the UV light emission patterns of the respective UV LED chips can be adjusted based at least partly on a shape of the area to be sterilized.

In some implementations, the UV sterilizer further includes a lens replaceably disposed over at least one of the UV LED chips, the lens having a depression formed on a surface of the lens, wherein at least one of the UV light emission patterns can be adjusted based on a shape of the depression.

In another aspect, a UV sterilizer is provided to comprise: a main body including a hollow space at an upper portion of the main body and having a first UV LED chip; and a sub-body detachably arranged inside the hollow space of the main body and having a second UV LED chip, wherein the sub-body is configured to perform sterilization using UV light emitted from the second UV LED chip detached from and independent of the main body.

As described above, embodiments of the disclosed technology provide at least a UV sterilizer in which a body is freely movable among various target spaces to be sterilized. In addition, a light emission pattern can be controlled according to a shape of the sterilization target space by employing a lens that can adjust light emission or distribution. Further, a main body and a sub-body can be detachably attached to each other to sterilize a variety of spaces regardless of a size. For example, the UV sterilizer can easily sterilize an internal space of a product having a small inlet as well as that of a product having a large inlet.

DETAILED DESCRIPTION OF THE EXEMPLARY EMBODIMENTS

Figure 1:
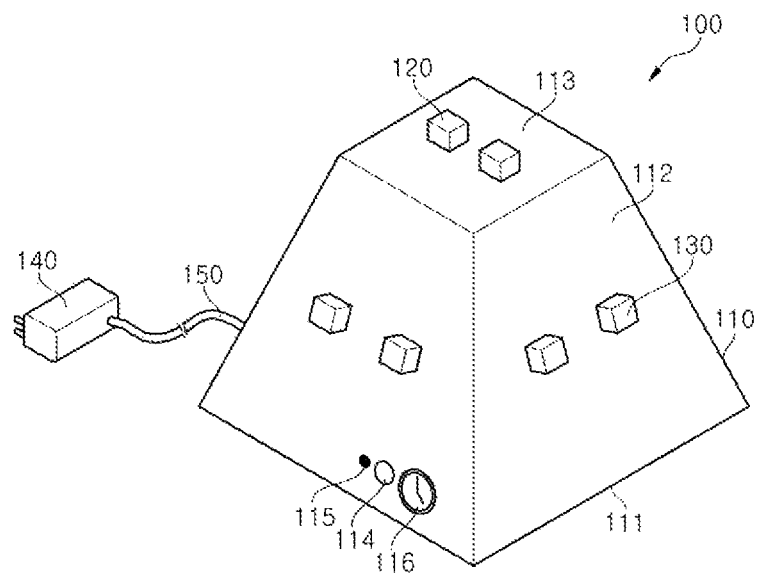
FIG. 1 is a schematic perspective view of an ultraviolet (UV) sterilizer according to one embodiment of the disclosed technology.

Hereinafter, exemplary embodiments of the disclosure of this patent document will be described in detail with reference to the accompanying drawings. The following embodiments are provided for illustrative purposes in an attempt to fully convey the scope of the disclosed technology to those skilled in the art. Accordingly, the disclosed technology is not limited to the embodiments disclosed herein and can also be implemented in different forms. In the drawings, certain dimensions such as widths, lengths, thicknesses, and the like of certain components may have been exaggerated for convenience. Throughout the specification, like reference numerals denote like elements having the same or similar functions.

FIG. 1 is a schematic perspective view of a UV sterilizer 100 according to one embodiment of the disclosed technology.

Referring to FIG. 1, the UV sterilizer 100 can include a body 110, first UV LED chips 120, second UV LED chips 130, a converter 140, and an electric wire 150.

The body 110 is structured to form a desired appearance of the UV sterilizer 100 and supports the first and second UV LED chips 120 and 130. The body 110 can include sidewalls 112, a top surface 113, and a bottom surface 111. The first UV LED chips 120 are provided or disposed on the top surface 113 of the body 110 and the second UV LED chips 130 are provided or disposed on the sidewalls 112 of the body.

The bottom surface 111 can be flat such that the body 110 is stably disposed on a flat plane. The sidewalls 112 can be inclined to have a gradually decreasing width toward the top surface 113. In other words, the body 110 can have transverse cross-sectional areas gradually decreasing from the bottom surface 111 to the top surface 113 of the body 110 such that the sidewalls 112 of the body 110 are inclined towards the top surface, for example.

Figure 2:
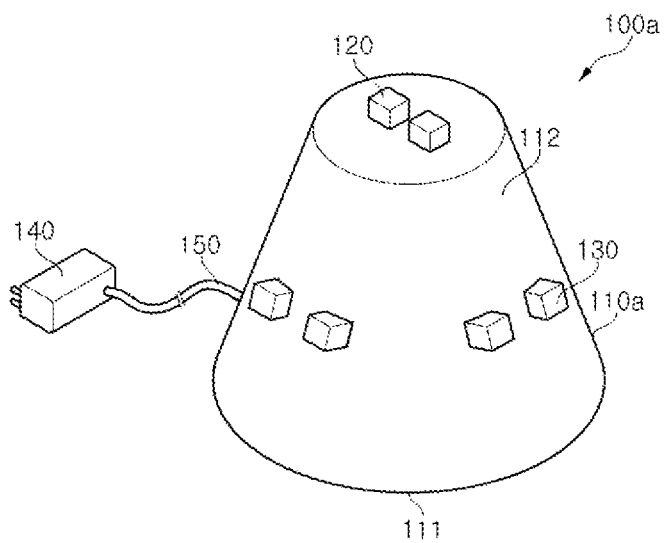
FIG. 2 is a schematic perspective view of a UV sterilizer according to one embodiment of the disclosed technology.

As shown in FIG. 1, the body 110 can have a desired shape such as a polygonal (e.g., quadrangular) frusto-pyramidal shape having a gradually decreasing width from the bottom surface 111 to the top surface 113. In this case, the body 110 has four sidewalls 112. However, the disclosed technology is not limited to the body 110 having the polygonal (e.g., quadrangular) frusto-pyramidal shape. For example, a body 110a having a frusto-conical shape can be employed for a UV sterilizer 100a, as shown in FIG. 2. Other shapes that enhance the universal applicability of the UV sterilizer in various spaces and appliances of different shapes and sizes are also contemplated and possible.

A tilt or incline angle of the sidewalls 112 can be selected within the range of, for example, 20 degrees to 80 degrees in reference to an orientation pattern of UV light directed upward from the body 110. For postural stability of the body 110, the height of the body 110 can be set to be smaller than the width of the bottom surface 111.

The body 110 can be provided with a power button 114 that turns on or off electric power supplied to the body 110, an illumination sensor 115 that senses ambient luminance to determine whether to turn on or off electric power, and a timer 116 that allows the UV sterilizer to operate for a preset period of time. The power button 114, the illumination sensor 115, or the timer 115 enables the UV sterilizer to operate without being exposed to UV light.

In one implementation, the power button 114 can be operated through a remote controller. In this case, the body 110 can further include a receiver (not shown) and a controller (not shown) to recognize signals from the remote controller and control operations of the body 110 in response to the recognized signals. When the body 110 includes the receiver and the controller, operations of the UV sterilizer can be remotely controlled without a user present at the sterilization location to avoid human exposure to UV light.

The converter 140 is an alternating current (AC) to direct current (DC) converter that converts AC power supplying voltage into DC power supplying voltage. The converter 140 converts household high-voltage AC power supplying voltage of 100 V or higher, for example 110 V or 220 V, into low-voltage DC power supplying voltage of 75 V or lower, for example, 5 V to 75 V. In some implementations, the converter 140 can convert AC power supplying voltage of 100 V or higher into DC power supplying voltage of 40 V or higher. When the converter 140 provides conversion to higher voltage DC power supply, the size of the converter 140 can be reduced and cost of the converter 140 can be saved.

The electric wire 150 connects the converter 140 to the body 110. The electric wire 150 transmits electric power and output from the converter 140 to the first and second UV LED chips 120, 130. The electric wire 150 has a structure in which an internal conductive wire is covered with an insulating material. The electric wire 150 can include a pair of conductive wires connected to positive and negative terminals, respectively.

In general, a thickness of an electric wire can be determined based on an element to which the electric wire is connected. When an electric wire (cable) is connected to a household AC power source, the electric wire has a relatively greater thickness to maintain stability and reliability in transmitting high-voltage AC current. However, in this embodiment, since the electric wire 150 is connected to the converter 140 converting household AC power supplying voltage into DC power supplying voltage of 75 V or lower, the thickness of the electric wire 150 is thinner than that of the cable connected to the household AC power source. Since the thickness of the electric wire 150 becomes reduced as compared to the cable connected to the household AC power source, the electric wire 150 can be advantageously applied to electric appliances while not requiring a large space.

Due to the reduced thickness or gauge of the electric wire 150 connected to the body 110, the UV sterilizer 100 can be disposed within an electronic appliance, such as a refrigerator, to perform sterilization with the door closed without affecting the ability to seal an internal space of the refrigerator in a normal or proper manner. In contrast, when a typical cable for transmitting household AC power is used, the cable having a greater thickness can prevent the door of the refrigerator from being properly closed and can cause an air passage through an incomplete seal.

Although the electric wire 150 has been described to be directly connected to the body 110, other implementations are also possible. In one implementation, the electric wire 150 can be attached to or detached from the body 110 through a connector (not shown). In another implementation, the electric wire 150 can be attached to or detached from the converter 140 through a connector (not shown).

The first and second UV LED chips 120, 130 can be the same type of UV LED chip or different types of UV LED chips. The first and second UV LED chips 120, 130 can be composed of or include UV LED chips emitting UV light in a wavelength band of 180 nm to 400 nm. In one example, the first and second UV LED chips 120, 130 can be composed of or include UV LED chips emitting UV-C in a wavelength band of 180 nm to 280 nm. In another example, the first and second UV LED chips 120, 130 can be composed of or include UV LED chips emitting UV light in a wavelength band of 250 nm to 280 nm. UV light in a wavelength band of 250 nm to 280 nm is effective in destroying and sterilizing DNA of microorganisms such as bacteria or viruses.

The first UV LED chips 120 are disposed on the top surface 113 of the body 110, and the second UV LED chips 130 are disposed on the sidewalls 112 of the body 110. As shown in FIG. 1, when the body 110 has a shape such as a polygonal (e.g., quadrangular) frusto-pyramidal shape, the second UV LED chips 130 can be disposed on each of the sidewalls 112. Light emitting surfaces of the second UV LED chips 130 disposed on the sidewalls 112 can be substantially parallel to surface of the sidewalls 112. However, it should be understood that the disclosed technology is not limited as described, and the orientation of the light emitting surfaces of the second UV LED chips 130 can be adjusted in various ways, as needed. In addition, according to one embodiment, the second UV LED chips 130 can be arranged at the same locations on the respective sidewalls 112. However, it should be understood that the disclosed technology is not necessarily limited as described and a different number of second UV LED chips 130 can also be arranged at different locations on the respective sidewalls 112.

In FIG. 1, two first UV LED chips 120 are arranged on the top surface of the body 110 and two second UV LED chips 130 are arranged on each of the sidewalls 112 of the body 110. However, it should be understood that the disclosed technology is not limited as described and the numbers of first and second UV LED chips 120, 130 can be selected in various ways.

In addition, although the first and second UV LED chips 120, 130 are shown and described to be arranged to have a shape of a chip as mounted on the body 110, the first and second UV LED chips 120, 130 can be arranged on the body 110 in a variety of shapes on the body 110. For example, the first and second UV LED chips 120, 130 can be mounted on a printed circuit board (PCB), and the PCB can be attached to the body 110. The electric wire 150 can be electrically connected to terminals of the PCB, and electric power can be supplied to the first and second UV LED chips 120, 130 via a circuit of the PCB. Further, the first and second UV LED chips 120, 130 can be mounted in the shape of a package on the PCB, without being limited to the chip shape.

The body 110 can include a control circuit (not shown) to drive and control the first and second UV LED chips 120, 130. The control circuit can be connected to the power button 115, the illumination sensor 115, and the timer 116 to control operations of the UV sterilizer 100 according to signals input to the control circuit. The control circuit can be driven or supplied with low-voltage DC power transmitted through the electric wire 150.

As long as the UV sterilizer 100 is supplied with electric power through the converter 140 and the electric wire 150, the UV sterilizer 100 can be used to sterilize a variety of spaces, without being limited to specific electronic appliances. For sterilization of an appliance, the body 110 of the UV sterilizer 100 can be disposed in any place or location available in the appliance, such as in a refrigerator, a washing machine, a humidifier, a sink, a wardrobe, a shoe rack, a bed, and the like. Electric power can be supplied not only through a household power outlet but also through a computer. In this case, electric power can be supplied using a universal serial bus (USB) interface. Other applications are possible include in a vehicle. For example, the UV sterilizer 100 can be disposed in the vehicle to sterilize an internal space of the vehicle while receiving electric power through a cigarette lighter jack for a vehicle.

Although the UV sterilizer 100 has been described to receive electric power through the electric wire 150, the UV sterilizer 100 can use a rechargeable battery instead of the electric wire 150. Using the rechargeable battery can increase the portability of the body 110.

Figure 3:
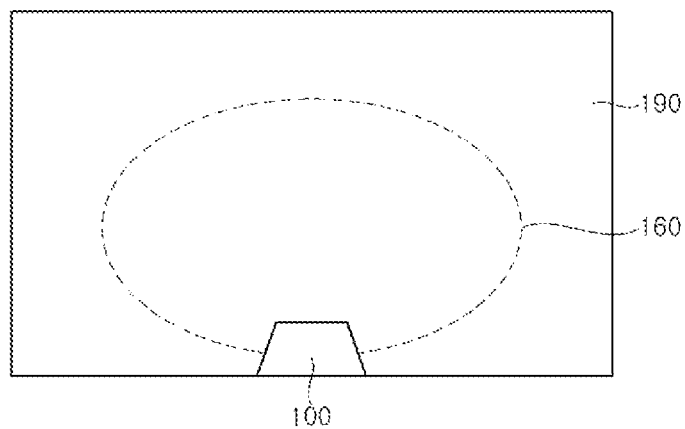
FIG. 3 shows a light emission pattern of the UV sterilizer according to one embodiment of the disclosed technology.

FIG. 3 shows an exemplary light emission pattern associated with an orientation pattern of the UV LED chips 120 and 130 of the UV sterilizer according to one embodiment of the disclosed technology.

The first and second UV LED chips 120 and 130 emit UV light upward from the UV sterilizer 100. A light emission pattern of the UV light emitted by the UV LED chips 120 and 130 is represented by the sum of distribution of the UV light emitted from the first UV LED chips 120 disposed on the top surface 113 of the body 110 and distribution of the UV light emitted from the second UV LED chips 130 disposed on the sidewalls 112 of the body 110. Since the second UV LED chips 130 are arranged on the sidewalls of the body 110, the overall shape of the light emission pattern 160 of the UV sterilizer 100 can have a relatively flat and oval shape. Based at least partly on the overall shape of the light emission pattern 160, the UV sterilizer 100 can be suited to sterilize a space 190 having a width greater than a height, as shown in FIG. 3.

Figure 4:
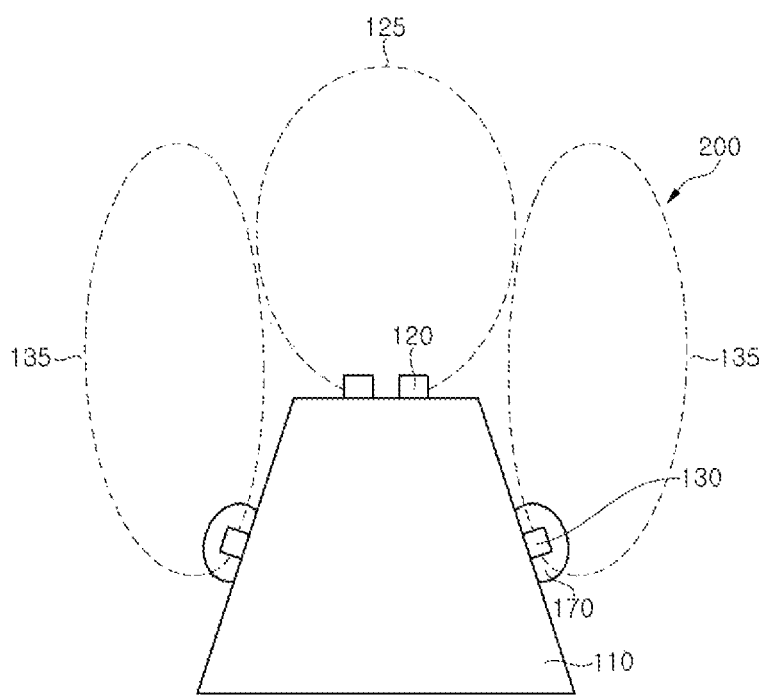
FIG. 4 is a schematic sectional view of a UV sterilizer including a lens according to one embodiment of the disclosed technology.
Figure 5:
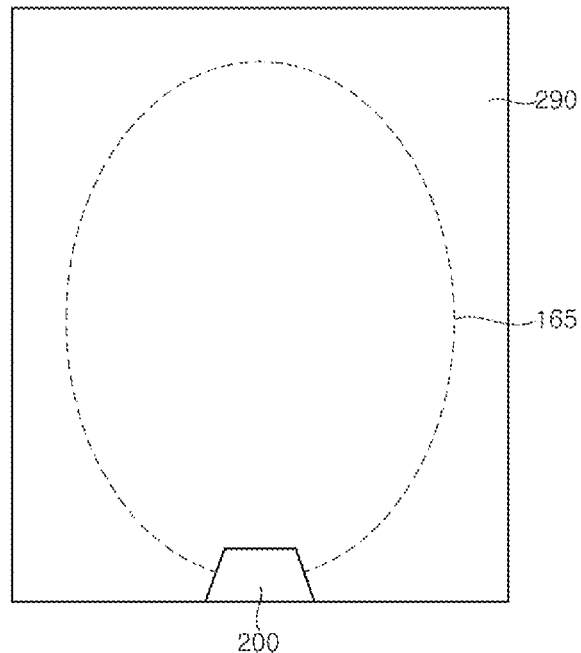
FIG. 5 shows a light emission pattern of the UV sterilizer shown in FIG. 4.

FIG. 4 is a schematic sectional view of an exemplary UV sterilizer 200 including a lens according to another embodiment of the disclosed technology, and FIG. 5 shows an exemplary light emission pattern of the UV sterilizer 200 shown in FIG. 4.

Referring to FIG. 4, the UV sterilizer 200 is substantially similar to the UV sterilizer 100 described with reference to FIG. 1 with a few differences. For example, the UV sterilizer 200 includes lenses 170. The lenses 170 can be disposed on second UV LED chips 130, respectively, to change emission or distribution pattern of UV light emitted from the second UV LED chips 130. For example, the second UV LED chips 130 can emit UV light at a beam spread of about 120 degrees with respect to a direction substantially perpendicular to sidewalls 112 without any lenses 170. The emission or distribution pattern of the UV light is changed by the lenses 170. For example, as shown by dotted lines 135 in FIG. 4, the emission or distribution pattern has been changed by the lenses 170 to be directed more upward than laterally from the UV sterilizer 200. A dotted line 125 schematically represents the emission or distribution pattern of UV light emitted from first UV LED chips 120.

An exemplary light emission or distribution pattern 165 shown in FIG. 5 can be obtained by the sum of the emission or distribution patterns of the UV light emitted from the first UV LED chips 120 as shown by the dotted line 125, and the emission or distribution pattern of the UV light emitted through the lenses 170 from the second UV LED chips 130 as shown by the dotted lines 135. The light emission or distribution pattern 165 has an elongated shape projecting upward from the UV sterilizer 200. Thus, based at least partly on the upwardly elongated shape of the light emission or distribution pattern 165, the sterilizer can be suited to sterilize a space 290 having a greater height than a width.

Figure 6:
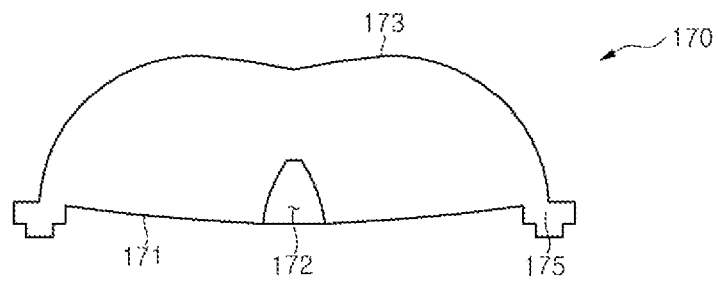
FIG. 6 is a schematic sectional view showing an example of the lens shown in FIG. 4.

FIG. 6 is a sectional view showing one example of a lens that can be used in the above-described embodiment.

Referring to FIG. 6, the lens 170 has a shape capable of changing a path of UV light emitted from the second UV LED chips 130. For example, the lens 170 can have a lower surface 171 surrounding a depression 172 and an upper surface 173. The lower surface 171 can be flat or inclined, as shown in FIG. 6. A path of light incident upon the depression 172 can be diversely changed to achieve a target direction by controlling the shapes of the depression 172, the upper surface 173, or both.

The lens 170 can include one or more supporting members, such as legs 175 through which the lens 170 is coupled to a body 110. When the second UV LED chips 130 are mounted on a PCB, the PCB can have a coupling mechanism for coupling the lens 170. Such coupling mechanism may include, for example, coupling recesses. In this case, the legs 175 can be coupled to the PCB by fitting into the coupling recesses of the PCB.

The lens 170 can be freely detached from the body 110 and replace by a lens having a different shape according to a desired purpose of use.

Although the lens 170 has been explained to be disposed on each of the second UV LED chips 130, an appropriate lens can also be disposed on each of the first UV LED chips 120 as needed.

Figure 7:
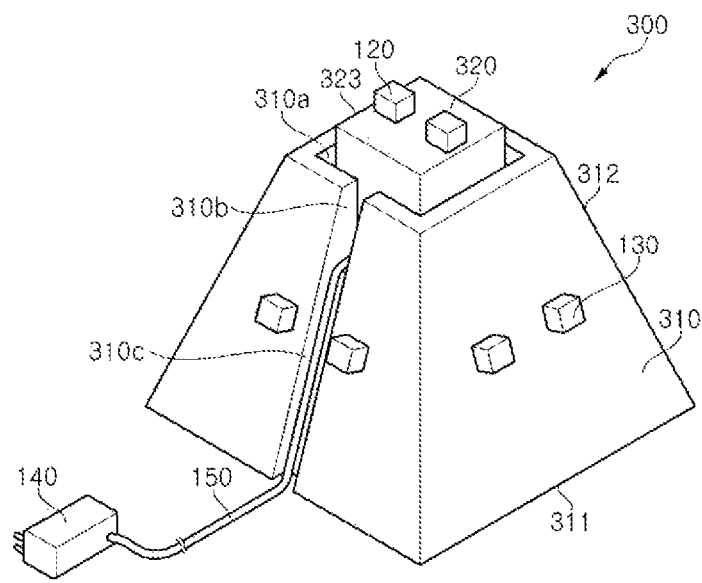
FIG. 7 is a schematic perspective view of a UV sterilizer according to one embodiment of the disclosed technology.
Figure 8:
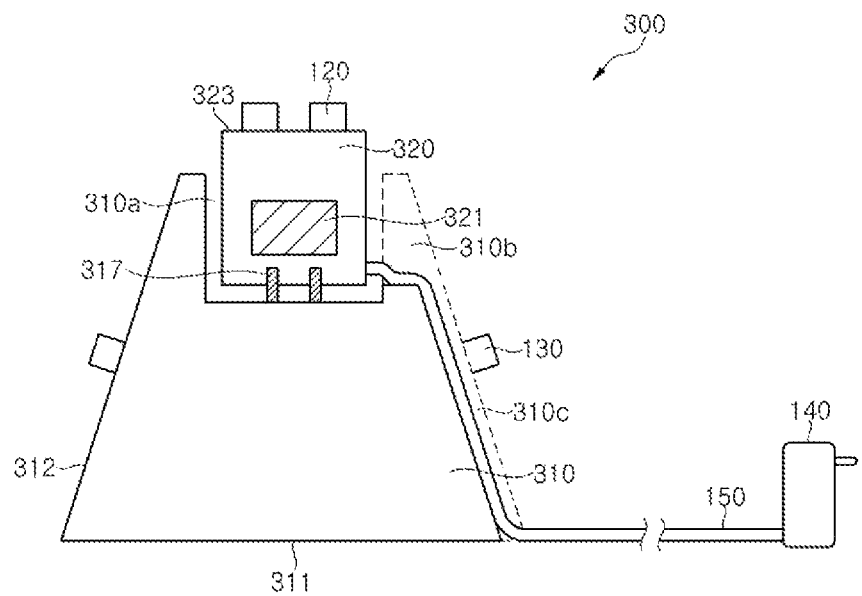
FIG. 8 is a schematic sectional view of the UV sterilizer shown in FIG. 7.

FIG. 7 is a schematic perspective view of an exemplary UV sterilizer according to yet another embodiment of the disclosed technology, and FIG. 8 is a schematic sectional view of the UV sterilizer shown in FIG. 7.

A UV sterilizer 300 of FIGS. 7 and 8 is substantially similar to the UV sterilizer described with reference to FIG. 1 with a few differences. For example, the UV sterilizer 300 includes a main body 310 and a sub-body 320.

The main body 310 has a bottom surface 311 and sidewalls 312. The bottom surface 311 and the sidewalls 312 are substantially similar to the bottom surface 111 and the sidewalls 112 described with reference to FIG. 1, and thus detailed descriptions of the various surfaces of the main body 310 have been omitted to avoid repetition. Second UV LED chips 130 are arranged on the sidewalls 312 of the main body 310.

The main body 310 can have a recess 310a, a slot 310b, and a groove 310c. The recess 310a can be formed at an upper end or top surface of the main body 310, and electric terminals 317 such as pogo pins can be disposed within the recess 310a.

The slot 310b can be formed on one sidewall 312 of the main body 310. The slot 310b can be formed to have a predetermined depth from the upper end of the main body 310, and the recess 310a is exposed to outside through the slot 310b. The groove 310c is formed on an outer surface of the main body 310. The groove 310b can be formed on the sidewall 312 to extend downward from the slot 310b.

The sub-body 320 is inserted into the recess 310a and electrically connected to the electric terminals 317. First UV LED chips 120 are arranged on an upper surface 323 of the sub-body 320.

The sub-body 320 can have coupling recesses (see reference numeral 325 of FIG. 9) into which the electric terminals 317 are fitted. The electric terminals 317, such as pogo pins, formed on the main body 310 are fitted into the coupling recesses 325 of the sub-body 320, whereby the sub-body 320 can be aligned with the main body 310. Electric connection between the main body 310 and the sub-body 320 can be implemented in various manners without being limited to the use of the pogo pins. For example, a variety of electric connection terminals including electric terminals using tension may be used for electric connection between the main body 310 and the sub-body 320.

The sub-body 320 can further include a magnet 321 disposed inside or outside of the sub-body 320. The magnet 321 is not limited to a specific type and can be a permanent magnet or electromagnet.

The sub-body 320 can be detachable from the main body 310. Thus, the first and second UV LED chips 120 and 130 can be simultaneously driven by coupling the main body 310 and the sub-body 320, or only the first or second UV LED chips 120 or 130 can be driven by detaching the sub-body 320 from the main body 310. In one embodiment, the sub-body 320 can have a desired shape including a cylindrical or quadrangular prismatic shape.

An electric wire 150 can be connected to the sub-body 320 in the manner as shown in FIGS. 7 and 8. When the sub-body 320 is coupled to the main body 310, the electric wire 150 can enter the recess 310a through the slot 310b. In addition, one portion of the electric wire 150 can be received in the groove 310c so as not to block UV light emitted from the second UV LED chips 130.

Although the electric wire 150 is shown to be connected to the sub-body 320, the disclosed technology is not limited to the described implementation. The electric wire 150 can also be connected to the main body 310. Each of the main body 310 and the sub-body 320 can be provided with terminals to which the electric wire 150 can be connected, or the electric wire 150 can be connected to the main body 310 or the sub-body 320 using a connector, as needed.

Figure 9:
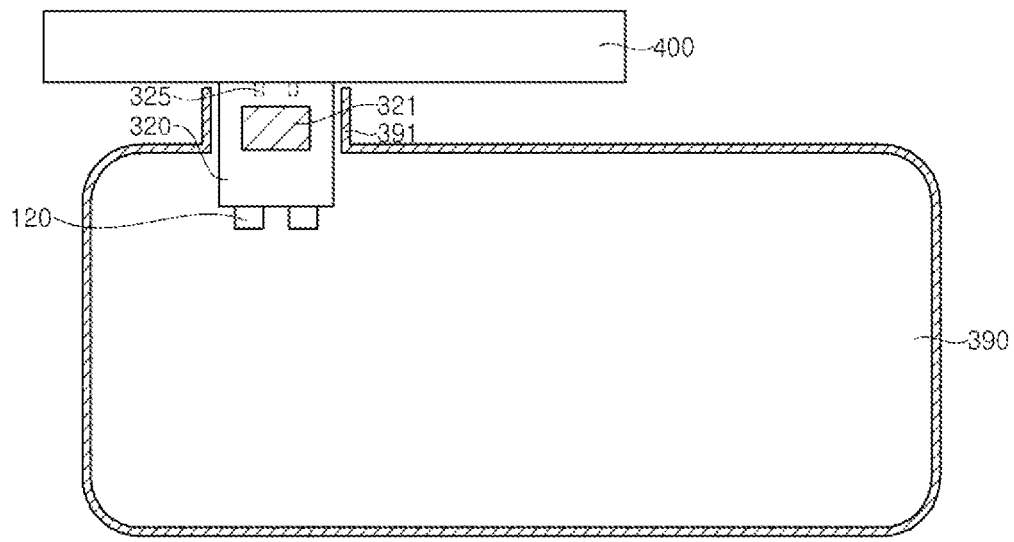
FIG. 9 is a schematic sectional view showing a use example of the sub-body shown in FIG. 7.

FIG. 9 is a schematic sectional view showing an exemplary use of the sub-body 320 shown in FIG. 7.

Referring to FIG. 9, the sub-body 320 sterilizes an internal space of a container 390 having an inlet 391. The container 390 can be a water storage tank used in, for example, a humidifier, or other types of containers. Since the inlet 391 has a smaller size than the internal space of the container 390, the body 110 shown in FIG. 1 cannot be disposed in the internal space of the container 390.

In this embodiment, by using the sub-body 320 detached from the main body 310, the internal space of the container 390 is sterilized. That is, as shown in FIG. 9, the sub-body 320 is detached from the main body 310 and then, inserted into the inlet 391 of the container 390. The inlet 391 can have a variety of shapes according to the type of the container 390, and the sub-body 320 can have a shape corresponding to the inlet having various shapes. For example, the sub-body 320 may have a cylindrical shape. As the first UV LED chips 120 enter the internal space of the container 390, sterilization function can be carried out for the container 390 using UV light emitted from the first UV LED chips 120.

The sub-body 320 can be attached to a support member 400 such as a metal rod in order to prevent the sub-body 320 from falling into the internal space of the container 390. The sub-body 320 can be attached to the support member 400 using a magnet 321. The magnet 321 enables the sub-body 320 to be easily attached to and detached from the support member 320. However, it should be understood that the disclosed technology is not limited to the magnet and other coupling members, such as hooks or tongs, can also be used to temporarily couple the sub-body 320 and the support member 400.

According to this embodiment, the sub-body 320 can be detached from the main body 310. When sterilizing a target space large enough to accommodate both the main body 310 and the sub-body 320, the UV sterilizer can perform sterilization while coupling the main body 310 and the sub-body 320. When a space to be sterilized is small and cannot accommodate both the main body 310 and the sub-body 320, the UV sterilizer can perform sterilization while the sub-body 320 is detached from the main body 310. A space having a small inlet, such as in a container can be easily sterilized using the sub-body 320 detached from the main body 310.

In this embodiment, when the conductive support member 400 such as a metal rod is used, it is necessary to prevent short circuit of connection terminals of the sub-body 320, which may be caused by the support member 400. To this end, connection parts of the sub-body 320 are advantageously disposed within the coupling recesses 325.

Figure 10:
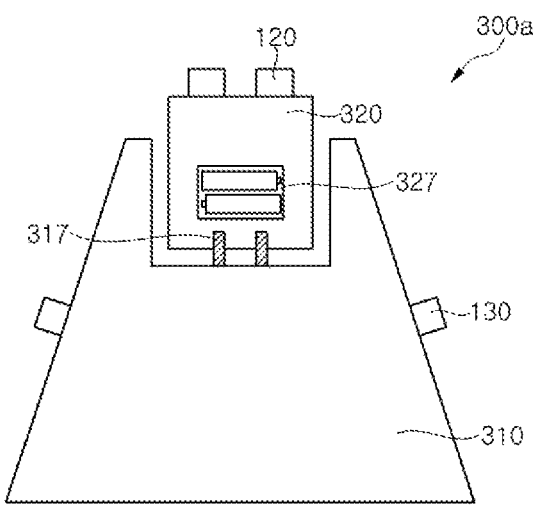
FIG. 10 is a schematic sectional view of a UV sterilizer according to one embodiment of the disclosed technology.

FIG. 10 is a schematic sectional view of an exemplary UV sterilizer 300a according to yet another embodiment of the disclosed technology.

Referring to FIG. 10, the UV sterilizer 300a according to this embodiment is substantially similar to the UV sterilizer 300 described with reference to FIGS. 7 and 8 with a few difference. For example, batteries 327 are mounted to a sub-body 320 instead of the electric wire 150 and the converter 140.

The batteries 327 can be single-use primary cells or rechargeable secondary cells. In this embodiment, the electric wire 150 and the converter 140 as shown in FIG. 7 are not required, and the sub-body 320 can be provided with a connection member (not shown) to which a charger is connected to recharge the batteries 327. In addition, when the batteries 327 are recharged while being separated from the sub-body 320, the connection member can also be omitted in the sub-body 320.

Although the batteries 327 are embedded in the sub-body 320 in this embodiment, the batteries 327 can also be embedded in the main body 310.

Although the various embodiments of the disclosed technology have been described above, the embodiments are provided to help with comprehension of the disclosed technology and various changes and modifications can be made to the embodiments. In addition, the technical features described in the respective embodiments can be applied to other embodiments without departing from the spirit and scope of the disclosed technology.

LIST OF REFERENCE NUMERALS 100, 100a, 200, 300, 300a: UV sterilizer
110, 110a: Body
111, 311: Bottom surface
112, 312: Sidewall
113, 323: Top surface
114: Power button
115: Illumination sensor
116: Timer
120: First UV LED chips
130: Second UV LED chips
140: Converter
150: Electric wire
160, 165: Light emission pattern
170: Lens
190, 290: Sterilization target space
310: Main body
310a: Recess
310b: Slot
310c: Groove
320: Sub-body
321: Magnet
325: Coupling recess
327: Battery
390: Container
391: Inlet

What is claimed is:
1. A UV sterilizer comprising:
a body including a top surface and a sidewall;
at least one first UV LED chip disposed on the top surface of the body; and
at least one second UV LED chip disposed on the sidewall of the body,
wherein the body has cross-sectional areas gradually decreasing toward the top surface, the sidewall is inclined, and a light emitting surface of the second UV LED chip is substantially parallel to a surface of the sidewall.

2. The UV sterilizer of claim 1, wherein the body includes a main body and a sub-body detachably coupled to the main body.

3. The UV sterilizer of claim 2, wherein the main body has a recess for accommodating the sub-body, the sub-body is electrically connected to the main body within the recess of the main body, the first UV LED chip is disposed on the sub-body, and the second UV LED chip is disposed on the main body.

4. The UV sterilizer of claim 3, wherein the sub-body has a smaller width than the main body.

5. The UV sterilizer of claim 4, wherein the sub-body has a polygonal prismatic shape or a cylindrical shape.

6. The UV sterilizer of claim 2, further including:
an electric wire connected to the sub-body and supplying DC power to the first and second UV LED chips.

7. The UV sterilizer of claim 6, further including:
a converter that converts high-voltage AC power into low-voltage DC power,
wherein the converter is disposed outside the sub-body and the electric wire is connected to the converter.

8. The UV sterilizer of claim 6, wherein the main body has a slot passing through sidewall of the main body and connected to the recess, and the electric wire is received in the slot when the sub-body is coupled to the main body.

9. The UV sterilizer of claim 8, wherein the main body further includes a groove formed on an outer surface of the sidewall of the main body and extending from the slot.

10. The UV sterilizer of claim 2, further including:
a battery disposed inside the sub-body and supplying DC power to the first and second UV LED chips.

11. The UV sterilizer of claim 2, wherein the sub-body includes a magnet.

12. The UV sterilizer of claim 1, wherein the body further includes a receiver and a controller, and the receiver receives signals from a remote controller separated from the body.

13. The UV sterilizer of claim 1, further including:
an electric wire supplying DC power voltage of 75 V or lower to the first and second UV LED chips,
wherein the electric wire has a smaller thickness than a household power supply cable.

14. The UV sterilizer of claim 1, further including:
a battery supplying DC power to the first and second UV LED chips.

15. The UV sterilizer of claim 1, further including:
a lens changing distribution of light e of the second UV LED chip.

16. The UV sterilizer of claim 15, wherein the lens includes a supporting member.

17. The UV sterilizer of claim 15, wherein the lens is detachable from the body.

18. The UV sterilizer of claim 1, wherein the body has a polygonal frusto-pyramidal shape or a frusto-conical shape.

19. A UV sterilizer comprising:
a body having a top surface and a sidewall shaped to fit in an area to be sterilized;
an UV LED chip disposed on a top surface of the body and structured to emit UV light having an emission pattern to distribute the emitted UV light within the area to be sterilized; and
another UV LED chip disposed on a sidewall of the sub-body and structured to emit another UV light having another emission pattern to distribute the other emitted light within the area to be sterilized,
wherein at least one of the UV light emission patterns of the respective UV LED chips can be adjusted based at least partly on a shape of the area to be sterilized.

20. The UV sterilizer of claim 19, further including:
a lens replaceably disposed over at least one of the UV LED chips, the lens having a depression formed on a surface of the lens,
wherein at least one of the UV light emission patterns can be adjusted based on a shape of the depression.

21. A UV sterilizer comprising:
a main body including a hollow space at an upper portion of the main body and supporting one or more first UV LED chips that emit UV light to cause sterilization, wherein the hollow space provides a space including one or more electric terminals; and
a sub-body detachably arranged inside the hollow space of the main body and supporting one or more second UV LED chips that emit UV light to cause sterilization, wherein the sub-body includes one or more recesses that can receive the one or more electric terminals in the hollow space of the main body when the sub-body is attached inside the hollow space to supply electric power to the one or more second UV LEDs in the sub-body,
wherein the sub-body is configured to perform sterilization using UV light emitted from the one or more second UV LED chips when detached from and independent of the main body.

22. The UV sterilizer of claim 21, wherein the sub-body includes a magnet that allows the sub-body to magnetically attach to another support when detached from the main body.

23. The UV sterilizer of claim 21, wherein the electric terminal includes a pogo pin.

* * * * *